(12) United States Patent
Ando et al.

(10) Patent No.: US 9,895,296 B2
(45) Date of Patent: *Feb. 20, 2018

(54) COSMETIC PREPARATION

(71) Applicant: Shin-Etsu Chemical Co., Ltd., Tokyo (JP)

(72) Inventors: Yuji Ando, Annaka (JP); Shinji Irifune, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/441,028

(22) PCT Filed: Nov. 28, 2013

(86) PCT No.: PCT/JP2013/082073
§ 371 (c)(1),
(2) Date: May 6, 2015

(87) PCT Pub. No.: WO2014/084319
PCT Pub. Date: Jun. 5, 2014

(65) Prior Publication Data
US 2015/0290091 A1    Oct. 15, 2015

(30) Foreign Application Priority Data
Nov. 30, 2012  (JP) ................ 2012-261990

(51) Int. Cl.
| C08G 77/16 | (2006.01) |
| A61K 8/06 | (2006.01) |
| A61Q 5/02 | (2006.01) |
| A61Q 5/12 | (2006.01) |
| A61K 8/892 | (2006.01) |
| A61Q 5/00 | (2006.01) |
| A61Q 5/06 | (2006.01) |
| A61Q 19/00 | (2006.01) |

(52) U.S. Cl.
CPC ............. *A61K 8/068* (2013.01); *A61K 8/06* (2013.01); *A61K 8/892* (2013.01); *A61Q 5/00* (2013.01); *A61Q 5/02* (2013.01); *A61Q 5/06* (2013.01); *A61Q 5/12* (2013.01); *A61Q 19/00* (2013.01); *A61K 2800/21* (2013.01); *A61K 2800/594* (2013.01); *A61K 2800/805* (2013.01)

(58) Field of Classification Search
None
See application file for complete search history.

(56) References Cited

U.S. PATENT DOCUMENTS

| 2,891,920 A | 6/1959 | Hyde et al. |
| 3,294,725 A | 12/1966 | Findlay et al. |
| 3,958,581 A | 5/1976 | Abegg et al. |
| 3,962,418 A | 6/1976 | Birkofer |
| 4,009,256 A | 2/1977 | Nowak, Jr. et al. |
| 5,747,016 A * | 5/1998 | Yui ............... A61K 8/898 424/401 |
| 6,232,396 B1 | 5/2001 | Dong et al. |
| 8,475,777 B2 | 7/2013 | Rautschek |
| 2001/0012872 A1 | 8/2001 | Dong et al. |
| 2004/0138373 A1 | 7/2004 | Hamachi et al. |
| 2007/0276087 A1 | 11/2007 | Paul |
| 2012/0171147 A1 | 7/2012 | Rautschek |
| 2014/0093547 A1 | 4/2014 | Cauvin et al. |
| 2014/0378553 A1 | 12/2014 | Ando |

FOREIGN PATENT DOCUMENTS

| CN | 103687896 A | 3/2014 |
| DE | 196 29 621 A1 | 1/1997 |
| EP | 2 706 080 A1 | 3/2014 |
| JP | 34 2041 | 4/1959 |
| JP | 41 13995 | 8/1966 |
| JP | 11 71522 | 3/1999 |
| JP | 3145394 | 3/2001 |
| JP | 2001 106788 | 4/2001 |
| JP | 2003 12930 | 1/2003 |
| JP | 2003 252994 | 9/2003 |
| JP | 2007 297533 | 11/2007 |
| JP | 2014-512418 A | 5/2014 |
| WO | WO 2006/081978 A1 | 8/2006 |
| WO | 2011 032824 | 3/2011 |
| WO | 2012 119916 | 9/2012 |
| WO | 2013 153833 | 10/2013 |

OTHER PUBLICATIONS

JP 2001-106788 Machine Translation (2001) pp. 1-8.*
Office Action dated Jul. 21, 2016 in the corresponding Chinese Patent Application No. 201380060065.9 (with Partial English Translation).
"CFTA: Cosmetic Ingredient Dictionary, Second Edition", The Cosmetic, Toiletry and Fragrance Association, Inc., (1997), Total 524 Pages.
Caelles, et al., "Anionic and Cationic Compounds in Mixed Systems", Cosmetics & Toiletries, vol. 106, (Apr. 1991), pp. 49-54.
OSS, "Coacervation, Complex-Coacervation and Flocculation", J. Dispersion Science and Technology, vol. 9(5,6), (1988-89), pp. 561-573.

(Continued)

*Primary Examiner* — Dennis J Parad
*Assistant Examiner* — Lyndsey Beckhardt
(74) *Attorney, Agent, or Firm* — Oblon, McClelland, Maier & Neustadt, L.L.P.

(57) ABSTRACT

Provided is a cosmetic preparation superior in stability and feel. The cosmetic preparation contains an (a) organopolysiloxane emulsion in an amount of not smaller than 0.1% by mass. This organopolysiloxane emulsion is obtained through emulsion polymerization and contains octamethylcyclotetrasiloxane in an amount of not larger than 1,000 ppm by mass.

6 Claims, No Drawings

(56) References Cited

OTHER PUBLICATIONS

Burgess, "Practical Analysis of Complex Coacervate Systems", Journal of Colloid and Interface, vol. 140, No. 1, (Nov. 1990), pp. 227-238.
International Search Report dated Feb. 25, 2014 in PCT/JP13/082073 Filed Nov. 28, 2013.
Office Action dated Jun. 7, 2016 in Japanese Patent Application No. 2014-549898 (with English translation).
Extended European Search Report dated Jun. 27, 2016 in Patent Application No. 13859162.3.

* cited by examiner

COSMETIC PREPARATION

CROSS REFERENCE TO RELATED APPLICATIONS

The present application is a 35 U.S.C. § 371 national stage patent application of International patent application PCT/JP2013/082073, filed on Nov. 28, 2013, published as WO/2014/084319 on Jun. 5, 2014, the text of which is incorporated by reference, and claims the benefit of the filing date of Japanese application no. 2012-261990, filed on Nov. 30, 2012, the text of which is also incorporated by reference.

TECHNICAL FIELD

The present invention relates to a cosmetic preparation capable of preventing a feel and stability thereof from being impaired due to low molecular cyclosiloxanes. The present invention also relates to a hair cosmetic preparation capable of preventing a stability, feel and foaming property thereof from being impaired.

BACKGROUND ART

Silicone oils are widely used in cosmetic preparations, since they are colorless, odorless and chemically and physiologically inactive. Particularly, high-viscosity organopolysiloxanes are often used in hair cosmetic preparations, since they are capable of adhering to the hair in a favorable manner.

However, when directly emulsifying a high-viscosity organopolysiloxane, the average particle diameter of the emulsion particles can only be as small as about several micrometers, and a finer average particle diameter cannot be easily obtained, thus resulting in a low emulsion stability.

For this reason, various studies have been made on a method for producing an emulsion through emulsion polymerization, for the purpose of obtaining fine emulsion particles and thus improving the stability of the emulsion. For example, there has been known a method for performing emulsion polymerization on an emulsified cyclic siloxane oligomer, using a strong acid or a strong base (Patent documents 1, 2 and 3). However, in each method, octamethylcyclotetrasiloxane will be produced in an emulsion in an amount of not smaller than 1,000 ppm by mass. Thus, when adding such emulsion to a cosmetic preparation, there occurs a problem that the stability and feel will be impaired.

Further, octamethylcyclotetrasiloxane has been considered as a substance of concern in recent years, and cosmetic preparations containing a restricted amount of octamethylcyclotetrasiloxane have been demanded.

PRIOR ART DOCUMENTS

Patent Document

Patent document 1: Japanese published examined application No. Sho 34-2041
Patent document 2: Japanese published examined application No. Sho 41-13995
Patent document 3: Japanese Patent No. 3145394

DISCLOSURE OF THE INVENTION

Problem to be Solved by the Invention

Therefore, it is an object of the present invention to provide a cosmetic preparation whose stability and feel are not impaired due to low molecular cyclosiloxanes; and a hair cosmetic preparation whose stability, feel and foaming property are not impaired.

Means to Solve the Problem

In view of the aforementioned facts, the inventors of the present invention have dedicated themselves to carrying out further studies. As a result, they found a method for producing an organopolysiloxane emulsion that is obtained through emulsion polymerization and contains octamethylcyclotetrasiloxane in an amount of not larger than 1,000 ppm by mass. That is, the inventors found that the abovementioned problems could be solved by a cosmetic preparation using the organopolysiloxane emulsion obtained through such method, which led to the completion of the invention.

Particularly, the present invention provides the following cosmetic preparations.

(i) A cosmetic preparation 1 containing an (a) organopolysiloxane emulsion in an amount of not smaller than 0.1% by mass, such (a) organopolysiloxane emulsion being obtained through emulsion polymerization and containing octamethylcyclotetrasiloxane in an amount of not larger than 1,000 ppm by mass.

(ii) The cosmetic preparation of (i), in which the (a) organopolysiloxane emulsion is obtained by emulsion-polymerizing an organopolysiloxane expressed by the following general formula (1).

$$HO(R^1{}_2SiO)_nH \qquad (1)$$

(In the formula, $R^1$ independently represents a hydrogen atom or a substituted or unsubstituted hydrocarbon group having 1 to 20 carbon atoms; n represents a number allowing the kinetic viscosity of the organopolysiloxane to become 3,000 to 100,000 mm²/s at 25° C.)

(iii) The cosmetic preparation of (i) or (ii), in which the (a) organopolysiloxane emulsion is prepared by:

(I) obtaining a first emulsion composition by emulsifying a mixture containing
  (A) an organopolysiloxane expressed by the following general formula (1) and containing octamethylcyclotetrasiloxane in an amount of not larger than 1,000 ppm by mass 100 parts by mass $$HO(R^1{}_2SiO)_nH \qquad (1)$$

(In the formula, $R^1$ independently represents a hydrogen atom or a substituted or unsubstituted hydrocarbon group having 1 to 20 carbon atoms; n represents a number allowing a kinetic viscosity of the organopolysiloxane to become 3,000 to 100,000 mm²/s at 25° C.)
  (B) a non-ionic surfactant 1 to 100 parts by mass
  (C) an anion surfactant 1 to 100 parts by mass
  (provided that a range of mass ratio of component (B): component (C)=1:99 to 65:35) and
  (D-1) water 1 to 10 parts by mass; and then
(II) adding no water or adding (D-2) not larger than 100,000 parts by mass of water; to the first emulsion composition, followed by performing emulsion polymerization in the presence of an (E) acid catalyst at a temperature lower than 40° C. (the acid catalyst is not required, provided that the (C) anion surfactant is capable of acting as a catalyst).

(iv) The cosmetic preparation of (ii) or (iii), in which the temperature for performing emulsion polymerization (iii) is −15 to 5° C.

(v) The cosmetic preparation of any one of (i) to (iv), in which. D4 occupies not smaller than 60% by mass of a total amount of D3 to D10 in the (a) organopolysiloxane emulsion obtained through emulsion polymerization.

(vi) The cosmetic preparation of any one of (i) to (v), in which the total amount of D3 to D10 in the (a) organopolysiloxane emulsion obtained through emulsion polymerization is not larger than 1,000 ppm by mass.

(vii) The cosmetic preparation of any one of (i) to (vi), in which the average particle diameter of the (a) organopolysiloxane emulsion is not larger than 300 nm. Here, the average particle diameter is a value of median diameter on volume bases.

(viii) The cosmetic preparation of any one of (i) to (vii) further comprises (b) a surfactant; and (c) a cationic polymer, in addition to (a).

(ix) The cosmetic preparation of any one of (i) to (viii) as a hair cosmetic preparation.

Effects of the Invention

According to the present invention, there can be obtained a cosmetic preparation whose stability and feel are not impaired due to low molecular cyclosiloxanes. Further, for hair treatment purpose, there can be obtained a hair cosmetic preparation whose stability, feel and foaming property are not impaired.

MODE FOR CARRYING OUT THE INVENTION

—Material—

At first, the materials and raw materials used in the present invention are described.

<(a) Organopolysiloxane Emulsion Obtained Through Emulsion Polymerization and Containing Octamethylcyclotetrasiloxane in an Amount of not Larger than 1,000 ppm by Mass>

This emulsion can, for example, be prepared using the following method.

That is, the emulsion can be prepared by first obtaining an O/W emulsion and then performing emulsion polymerization by adding an acid or base catalyst. Particularly, such O/W emulsion is obtained using an emulsifying agent and water and then an (A) organopolysiloxane that is expressed by the following general formula (1) and contains octamethylcyclotetrasiloxane in an amount of not larger than 1,000 ppm by mass.

(In the formula, $R^1$ independently represents a hydrogen atom or a substituted or unsubstituted hydrocarbon group having 1 to 20 carbon atoms; n represents a number allowing the kinetic viscosity of the organopolysiloxane to become 3,000 to 100,000 mm$^2$/s at 25° C.)

Specifically, the following method is preferred.

(I) A first emulsion composition is prepared by emulsifying a mixture containing:
(A) organopolysiloxane expressed by the following general formula (1) and containing octamethylcyclotetrasiloxane in an amount of not larger than 1,000 ppm by mass

(In the formula, $R^1$ and n are defined as above);
(B) non-ionic surfactant
(C) anion surfactant
(provided that the range of mass ratio of component (B): component (C)=1:99 to 65:35); and
(D-1) water.
(II) Water (D-2) is then either added or not added to the first emulsion composition, followed by performing emulsion polymerization in the presence of an (E) acid catalyst at the temperature of lower than 40° C. (such acid catalyst is not required, provided that (C) anion surfactant is capable of acting as a catalyst).

The emulsion thus obtained contains octamethylcyclotetrasiloxane in an amount of not larger than 1,000 ppm by mass.

Although the amount of this emulsion (a) added to a cosmetic preparation is not smaller than 0.1% by mass, it is preferred that such emulsion be added in an amount of 0.1 to 10% by mass; and it is more preferred that such emulsion be added in an amount of 0.2 to 3% by mass.

Further described in detail hereunder are the raw materials used in the abovementioned production method.
<(A) Organopolysiloxane>

(A) is an organopolysiloxane expressed by the aforementioned general formula (1) and containing octamethylcyclotetrasiloxane in an amount of not larger than 1,000 ppm by mass.

In the general formula (1), $R^1$ represents a hydrogen atom or a substituted or unsubstituted hydrocarbon group having 1 to 20 carbon atoms. Unsubstituted hydrocarbon groups having 1 to 20 carbon atoms include, for example, an alkyl group having 1 to 20 carbon atoms; a cycloalkyl group having 3 to 20 carbon atoms; an alkenyl group having 2 to 20 carbon atoms; an aryl group having 6 to 20 carbon atoms; and an aralkyl group having 7 to 20 carbon atoms. Specifically, such unsubstituted hydrocarbon groups include an alkyl group such as a methyl group, an ethyl group, a propyl group, a butyl group, a pentyl group, a hexyl group, a heptyl group, an octyl group, a nonyl group, a decyl group, a dodecyl group, a tetradecyl group, a hexadecyl group or an octadecyl group; a cycloalkyl group such as a cyclopentyl group or a cyclohexyl group; an alkenyl group such as vinyl or allyl; and an aryl group such as a phenyl group, a tolyl group or a naphthyl group. Substituted hydrocarbon groups having 1 to 20 carbon atoms include those obtained by partially substituting the hydrogen atoms in the abovementioned monovalent hydrocarbon groups having 1 to 20 carbon atoms with, for example, halogen atoms, amino groups, acryloxy groups, methacryloxy groups, epoxy groups, mercapto groups, carboxyl groups and hydroxyl groups. Preferably, hydrocarbon groups having 1 to 6 carbon atoms such as methyl groups, ethyl groups, propyl groups, butyl groups and phenyl groups are used. It is more preferred that not less than 80% by mass of all the $R^1$ be methyl groups.

In the general formula (1), n represents a value allowing the kinetic viscosity of the organopolysiloxane to become 3,000 to 100,000 mm$^2$/s at 25° C. When such viscosity is lower than 3,000 mm$^2$/s, emulsion polymerization needs to be performed for a longer period of time to endow the organopolysiloxane contained in the target emulsion with a desired viscosity, thereby causing more octamethylcyclotetrasiloxane to be produced as a byproduct during emulsion polymerization, thus negatively affecting the stability, feel and foaming property when added to a cosmetic preparation. Meanwhile, when such viscosity is exceedingly high, the target emulsion obtained shall exhibit an unfavorable stability, thus also resulting in an unfavorable stability when added to a cosmetic preparation. It is preferred that such viscosity be 3,000 to 50,000 mm$^2$/s. It is particularly preferred that such viscosity be 4,000 to 20,000 mm$^2$/s.
<Non-Ionic Surfactant as Component (B)>

Non-ionic surfactants as the component (B) include, for example, polyoxyalkylene alkyl ether; polyoxyalkylene alkyl phenol ether; polyoxyalkylene alkyl ester; polyoxyalkylene sorbitan alkyl ester; polyethylene glycol; polypropylene glycol; and diethylene glycol. Above all, an nonionic surfactant expressed by the following general formula is preferred.

$$R^2O(EO)_p(AO)_qH$$

(In this formula, $R^2$ represents a linear or branched alkyl group having 8 to 30 carbon atoms, EO represents an ethylene oxide group, and AO represents an alkylene oxide group having 3 to 6 carbon atoms. The sequence of each group may be random or in the form of blocks. Each of p and q independently represents an integer of 0 to 100, provided that p+q>0.)

Here, alkylene oxide groups represented by AO and having 3 to 6 carbon atoms include, for example, a propylene oxide group; a butylene oxide group; and a hexylene oxide group. It is particularly preferred that $R^2$ be a linear or branched alkyl group having 8 to 12 carbon atoms, and that each of p and q independently represent 0 to 25.

The component (B) can be used in an amount of 1 to 100 parts by mass to 100 parts by mass of the component (A). It is preferred that the component (B) be used in an amount of 2 to 25 parts by mass, and it is particularly preferred that the component (B) be used in an amount of 3 to 10 parts by mass. In fact, not only one kind, but two or more kinds of the component (B) may also be used in combination.

<Anion Surfactant as Component (C)>

Following are examples of an anion surfactant as the component (C).

An alkyl sulfuric acid or its salt expressed by

General formula (C-1):

$$R^3OSO_3M \qquad (C\text{-}1)$$

(In the formula, $R^3$ represents a linear or branched alkyl group having 6 to 30 carbon atoms; M represents a hydrogen atom, an alkali metal atom such as potassium and sodium, an alkali earth metal atom such as magnesium and calcium, an ammonium ion or a quaternary ammonium ion.)

An alkylbenzene sulfonic acid or its salt expressed by

General formula (C-2):

$$R^3\text{-Ph-}SO_3M \qquad (C\text{-}2)$$

(In the formula, $R^3$ and M are defined as those in formula (C-1).)

In formulas (C-1) and (C-2), it is preferred that $R^3$ be a linear or branched alkyl group having 6 to 12 carbon atoms; and that M be a hydrogen atom, an alkali metal atom such as potassium and sodium, an alkali earth metal atom such as magnesium and calcium, an ammonium ion or a quaternary ammonium ion.)

Specific examples of the alkyl sulfuric acid or its salt expressed by formula (C-1) include hexyl sulfuric acid, octyl sulfuric acid, decyl sulfuric acid, dodecyl sulfuric acid, tetradecyl sulfuric acid, cetyl sulfuric acid, octadecyl sulfuric acid and aralkyl sulfuric acid; alkali metal salts thereof (e.g. lithium salt, sodium salt and potassium salt); alkali earth metal salts thereof (e.g. magnesium salt and calcium salt); triethanol ammonium salts thereof; and ammonium salts thereof.

Specific examples of the alkylbenzene sulfonic acid or its salt expressed by formula (C-2) include hexylbenzene sulfonic acid, octylbenzene sulfonic acid, decylbenzene sulfonic acid, dodecylbenzene sulfonic acid, cetylbenzene sulfonic acid and myristylbenzene sulfonic acid; and the salts thereof.

An polyoxyalkylene alkyl ether sulfuric acid or polyoxyalkylene alkyl ether sulfuric acid ester salt expressed by General formula (C-3):

$$R^3O(EO)_n(AO)_mSO_3M \qquad (C\text{-}3)$$

(In the formula, $R^3$ represents a linear or branched alkyl group having 6 to 30 carbon atoms; M represents a hydrogen atom, an alkali metal atom such as potassium and sodium, an alkali earth metal atom such as magnesium and calcium, an ammonium ion or a quaternary ammonium ion; EO represents an ethylene oxide group; AO represents an alkylene oxide group having 3 to 6 carbon atoms. The sequence of each group may be random or in the form of blocks. Further, each of n and m independently represents an integer of 0 to 100, provided that n+m>0.)

Here, examples of the alkylene oxide group represented by AO and having 3 to 6 carbon atoms include a propylene oxide group, a butylene oxide group and a hexylene oxide group. Specific examples thereof include polyoxyethylene hexyl ether sulfuric acid, polyoxyethylene octyl ether sulfuric acid, polyoxyethylene decyl ether sulfuric acid, polyoxyethylene dodecyl ether sulfuric acid, polyoxyethylene tetradecyl ether sulfuric acid, polyoxyethylene cetyl ether sulfuric acid, polyoxyethylene octadecyl ether sulfuric acid and polyoxyethylene aralkyl ether sulfuric acid; alkali metal salts thereof (e.g. lithium salt, sodium salt and potassium salt); alkali earth metal salts thereof (e.g. magnesium salt and calcium salt); triethanol ammonium salts thereof; and ammonium salts thereof.

A polyoxyalkylene alkylphenyl ether sulfuric acid and polyoxyalkylene alkylphenyl ether sulfuric acid ester salt etc. expressed by General formula (C-4):

$$R^3\text{-Ph-}O(EO)_n(AO)_mSO_3M \qquad (C\text{-}4)$$

(In the formula, $R^3$, M, EO, AO, n and m are defined as those in formula (C-3).) Specific examples thereof include polyoxyethylene hexylphenyl ether sulfuric acid, polyoxyethylene octylphenyl ether sulfuric acid, polyoxyethylene decylphenyl ether sulfuric acid, polyoxyethylene dodecylphenyl ether sulfuric acid, polyoxyethylene cetylphenyl ether sulfuric acid and polyoxyethylene myristylphenyl ether sulfuric acid; alkali metal salts thereof (e.g. lithium salt, sodium salt and potassium salt); alkali earth metal salts thereof (e.g. magnesium salt and calcium salt); triethanol ammonium salts thereof; and ammonium salts thereof.

Other examples of the component (C) include salts (preferably, alkali metal salts or alkali earth metal salts) of higher fatty acids such as lauric acid, stearic acid, oleic acid and linolenic acid.

It is preferred that the amount of the component (C) used be 1 to 100 parts by mass to 100 parts by mass of the component (A). Further, it is more preferred that the component (C) be used in an amount of 2 to 25 parts by mass. Furthermore, it is particularly preferred that the component (C) be used in an amount of 3 to 10 parts by mass. In fact, not only one kind, but two or more kinds of the component (C) may also be used in combination.

In addition, it is preferred that the mass ratio of the component (B) to component (C) is in the range of (B):(C)= 1:99 to 65:35. A range of (B)/(C) beyond 1.86 will significantly decrease the reaction rate of emulsion polymerization. In view of improving the stability of the emulsion composition obtained, it is preferred that the mass ratio be (B):(C)=20:80 to 55:45; and particularly preferred that the mass ratio be (B):(C)=30:70 to 45:55.

<(D) Water>

In step (I), water is added as (D-1) and in an amount of 1 to 10 parts by mass to 100 parts by mass of (A). Here, if water is added in an amount greater than 10 parts by mass, it will be difficult to obtain a fine emulsion composition whose emulsion particles have an average particle diameter of not larger than 300 nm, thus decreasing the stability of the emulsion. Meanwhile, if water is added in an amount of smaller than 1 part by mass, it will be difficult to produce an O/W emulsion. It is preferred that water be added in an amount of 2 to 8 parts by mass to 100 parts by mass of (A). Further, it is particularly preferred that water is added in an amount of 4 to 6 parts by mass to 100 parts by mass of (A).

While water may or may not be added in step (II), it is added in an amount of not larger than 100,000 parts by mass to 100 parts by mass of (A), if added.

<(E) Acid Catalyst>

An acid catalyst as the component (E) may be added at any timing as long as it exists in the polymerization system during step (II) of emulsion polymerization. However, the component (E) needs not to be used, if the component (C) is capable of acting as an acid catalyst.

—Step (I)—

The first emulsion composition is obtained by emulsifying the components (A), (B), (C) and (D-1). Particularly, emulsification may be performed using an emulsifier such as a homodisper, a homomixer, a colloid mill, a line mixer, a versatile mixer, an ultra mixer, a planetary mixer and a Combi Mix®.

In this step, if the component (C) used is capable of acting as an acid catalyst or if the component (E) is added, condensation also takes place at the same time, thus requiring that emulsification be performed at a temperature lower than 40° C. When emulsification is performed at 40° C. or higher, a large amount of octamethylcyclotetrasiloxane may be produced. Therefore, it is preferred that emulsification be performed at a temperature lower than 15° C.; and it is particularly preferred that emulsification be performed at a temperature lower than 5° C.

In step (I), the components (A), (B), (C) and (D-1) are mixed well until the average particle diameter of the emulsion particles of the first emulsion composition has reached 300 nm or smaller, preferably 200 nm or smaller, particularly preferably 150 nm or smaller. The smaller the particle diameter of the first emulsion particles, the higher the polymerization rate becomes in step (II), thus leading to a shorter polymerization time. Further, since the average particle diameter of the emulsion particles of the first emulsion composition is 300 nm or smaller, the average particle diameter of the final emulsion particles obtained in the following step will also become 300 nm or smaller. It is preferred that the average particle diameter eventually be 200 nm or smaller, and it is particularly preferred that the average particle diameter eventually be 150 nm or smaller.

<Step (II)>

At the beginning of this step, water (D-2) is added in an amount of 0 to 100,000 parts by mass to 100 parts by mass of the component (A), followed by performing emulsion polymerization. That is, water is optionally added before performing emulsion polymerization, and may actually not be added. If added, water is added in an amount of not larger than 100,000 parts by mass. It is preferred that water be added in an amount of 0 to 1,000 parts by mass, and it is particularly preferred that water be added in an amount of 0 to 200 parts by mass.

In this way, in the case where water (D-2) is added to the first emulsion composition, emulsification equipment such as a high-pressure homogenizer can also be used later to further perform emulsification and dispersion.

Next, such emulsion composition is subjected to emulsion polymerization. It is preferred that this polymerization step be carried out at a temperature of lower than 40° C. and within 48 hours. If the polymerization step is carried out at 40° C. or higher, octamethylcyclotetrasiloxane may be produced in a large amount. Therefore, it is preferred that the polymerization step be performed at a temperature of lower than 15° C., more preferably at a temperature of not higher than 5° C., and particularly preferably at a temperature of −15° C. to 5° C. Further, a polymerization time longer than 48 hours may cause octamethylcyclotetrasiloxane to be produced in a large amount. For this reason, it is preferred that the polymerization time be within 1 to 30 hours, particularly 5 to 24 hours.

At that time, the absolute viscosity of the organopolysiloxane produced through emulsion polymerization is 300,000 to 20,000,000 mPa·s; and the amount of octamethylcyclotetrasiloxane contained in the emulsion is not more than 1,000 ppm by mass.

By performing emulsion polymerization in the presence of (E) acid catalyst, polymerization is facilitated such that the polymerization time can be shortened. While it is not required to add (E) acid catalyst to the polymerization system other than (C) anion surfactant if (C) itself is capable of acting as an acid catalyst, (E) acid catalyst may nevertheless be added.

According to the method for producing the emulsion composition of the present invention, the polymerization time is within 15 hours, normally within a range of 5 to 15 hours; and the absolute viscosity (25° C.) of the organopolysiloxane produced reaches 300,000 mPa·s or higher. It is preferred that, within 15 hours, such absolute viscosity reach 500,000 mPa·s or higher, more preferably 1,000,000 mPa·s, and particularly preferably 5,000,000 mPa·s or higher.

<Other Treatment>

After polymerization is over, the emulsion composition obtained is usually neutralized with a basic substance. Examples of such basic substance include sodium hydroxide; potassium hydroxide; sodium hydrogen carbonate; and an amine compound such as triethanol amine and triethyl amine.

At that time, not only water can be added to adjust the silicone concentration, but a preservative agent and/or an antifungal agent, for example, may also be added to improve the preserving property of the emulsion composition.

By adding an organopolysiloxane such as $R^1_3SiO(R^1_2SiO)_nSiR^1_3$ to the emulsion composition obtained in step (I) where emulsification is performed; the emulsion composition obtained in step (II) where emulsion polymerization is performed; or the emulsion composition obtained after neutralization, there can be obtained an organopolysiloxane whose terminals are blocked by inactive triorganosiloxy groups. Further, branched units and/or various functional groups can also be introduced into an organopolysiloxane chain obtained by adding an alkoxysilane such as $R^1_3Si(OR^4)_1$, $R^1_2Si(OR^4)_2$ and $R^1_1Si(OR^4)_3$. Here, as defined above, $R^1$ represents a substituted or unsubstituted hydrocarbon group having 1 to 20, preferably 1 to 6 carbon atoms. Examples of such hydrocarbon group include a methyl group, an ethyl group, a propyl group, a butyl group and a phenyl group. $R^4$ represents an identical or different alkyl group having 1 to 20 carbon atoms; or a hydrogen atom. n represents 0 to 100.

In the present invention, when D4 (octamethylcyclotetrasiloxane) occupies a total amount of D3 (hexamethylcyclotrisiloxane) to D10 (eicosamethylcyclodecasiloxane) by a ratio of not smaller than 60% by mass, the feel and stability are improved in the case of a cosmetic preparation; and the feel, stability as well as foaming property are improved in the case of a hair cosmetic preparation. The reason for that is because, as compared to D4, D5 (decamethylcyclopentasiloxane) to D10 more negatively affect the feel and stability of a cosmetic preparation; and the feel, stability as well as foaming property of a hair cosmetic preparation. It is preferred that D4 occupy the total amount of D3 to D10 by a ratio of not smaller than 70% by mass. For the same reason, each of D5 to D10 occupies the total amount of D3 to D10 by a ratio of not larger than 30% by mass, preferably not larger than 20% by mass.

Moreover, when the amount of D4 contained in (a) is larger than 1,000 ppm by mass, there will be a significant impact on the environment. And, when the amount of low molecular cyclosiloxanes other than D4 contained in (a) are large, the feel and stability of a cosmetic preparation will be significantly impaired. In the case of a hair cosmetic preparation, the feel, stability as well as foaming property will be impaired.

The amount of such low molecular cyclosiloxane is larger than 100 ppm by mass as for D3; larger than 300 ppm by mass as for D5; larger than 200 ppm by mass as for D6; and larger than 100 ppm by mass as for each of D7 to D10. Therefore, it is preferred that the amount of such low molecular cyclosiloxane be not larger than 50 ppm by mass as for D3; not larger than 200 ppm by mass as for D5; not larger than 150 ppm by mass as for D6; and not larger than 50 ppm by mass as for each of D7 to D10. Further, it is particularly preferred that the amount of such low molecular cyclosiloxane be not larger than 30 ppm by mass as for D3; not larger than 150 ppm by mass as for D5; not larger than 100 ppm by mass as for D6; and not larger than 20 ppm by mass as for each of D7 to D10.

In addition, while the amounts of such low molecular cyclosiloxanes of each of D3 to D10 are as those described above, it is preferred that a total amount thereof be not larger than 1,000 ppm. This is because the total amount greater than 1,000 ppm will impair the feel and stability of a cosmetic preparation.

Cosmetic Preparation Component
<(b) Surfactant>

Examples of surfactant that can be added to the cosmetic preparation of the present invention include non-ionic surfactant, anion surfactant, cationic surfactant and amphoteric surfactant.

Examples of non-ionic surfactant include lecithin derivatives, propylene glycol fatty acid ester, glycerin fatty acid ester, polyglyceryl fatty acid ester, polyoxyalkylene glycerin fatty acid ester, sorbitan fatty acid ester, polyoxyalkylene sorbitan fatty acid ester, polyoxyalkylene sorbitol fatty acid ester, polyoxyalkylene lanolin derivatives, polyoxyalkylene lanolin alcohol derivatives, polyoxyalkylene bees wax derivatives, polyoxyalkylene hydrogenated castor oil, polyoxyalkylene sterol, polyoxyalkylene hydrogenated sterol, polyoxyalkylene alkyl ether, polyoxyalkylene alkyl phenol ether, polyoxyalkylene glycol fatty acid ester, alkyl alkanolamide and alkyl polyglucoside. Here, polyoxyalkylene represents either polyoxyethylene or polyoxypropylene wherein the oxyethylene units and oxypropylene units in the molecule may be random or in the form of blocks. Further, an alkyl group usually has 6 to 30 carbon atoms, and may be either linear or branched, or even unsaturated.

Examples of anion surfactant include N-acylamino acid and its salt, alkylether carboxylic acid and its salt, polyoxyalkylene alkylether acetic acid and its salt, a fatty acid soap, alkyl phosphoric acid and its salt, polyoxyalkylene alkylether phosphoric acid and its salt, N-acyltaurine and its salt, alkyl sulfuric acid and its salt, polyoxyalkylene alkylether sulfuric acid and its salt, alkylbenzene sulfonic acid and its salt, polyoxyalkylene alkylbenzene sulfonic acid and its salt, α-olefin sulfonic acid and its salt, alkyl sulfosuccinic acid and its salt and polyoxyalkylene alkyl sulfosuccinic acid and its salt. Here, examples of salt include alkali metal salts, alkali earth metal salts and amine salts. Further, polyoxyalkylene represents either polyoxyethylene or polyoxypropylene wherein the oxyethylene units and oxypropylene units in the molecule may be random or in the form of blocks. Further, an alkyl group usually has 6 to 30 carbon atoms, and may be either linear or branched, or even unsaturated.

Examples of cationic surfactant include a quaternary ammonium halide such as alkyltrimethylammonium halide and dialkyldimethyl ammonium halide; alkoxypropyltrimethyl ammonium halide; benzalkonium halide; and alkylphosphorylated benzalkonium. Further, an alkyl group usually has 6 to 30 carbon atoms, and may be either linear or branched, or even unsaturated.

Examples of amphoteric surfactant include an aminoacetic acid betaine such as alkyldimethylaminoacetic acid betaine; an amine oxide such as alkyldimethyl amine oxide; alkylcarboxymethylhydroxyethyl imidazolinium betaine; alkyl fatty acid amide propyl betaine; alkylamidepropyl betaine; alkylglycinate; alkylcarboxyglycinate; alkylamphopropionate; alkylamidepropyl hydroxysultaine; acyltaurate; and acyl glutamate. Further, an alkyl group usually has 6 to 30 carbon atoms, and may be either linear or branched, or even unsaturated.

It is preferred that the amount of (b) added to a cosmetic preparation be not smaller than 0.1% by mass. In fact, not only one kind, but two or more kinds of (b) may also be used in combination.

<(c) Cationic Polymer>

A cationic polymer may be formed of a homopolymer or not less than two kinds of monomers. It is usually preferred that the molecular weight thereof be 5,000 to Ser. No. 10/000,000. Further, such cationic polymer has a cationic nitrogen-containing group such as a quaternary ammonium group, a cationized amino group or a mixture thereof.

The cation charge density is at least 0.1 meq/g, preferably not lower than 0.8 meq/g. The cation charge density is below 4 meq/g, preferably less than 3 meq/g, more preferably less than 2 meq/g. Such cation charge density is measured through Kjeldahl method, and should be within the aforementioned ranges under a desired pH employed, such pH usually being about 3 to 9, preferably 4 to 8.

A cationic nitrogen-containing group generally exists as a substituent group on the fraction of all the monomer units of a cationic polymer. Therefore, when a cationic polymer is not a homo polymer, it can contain a non-cationic monomer unit as a spacer. Such polymers are listed in "CTFA Cosmetic Ingredient Dictionary, 3rd edition."

Examples of an appropriate cationic polymer include a copolymer of a vinyl monomer having cationic amine or quaternary ammonium functionality; and a water-soluble spacer monomer such as (metha) acrylamide, alkyl (metha) acrylamide, dialkyl (metha) acrylamide, alkyl (metha) acrylate, vinyl caprolactone and vinyl pyrrolidone. These alkyl and dialkyl substituted monomers contain preferably C1-C7 alkyl groups, more preferably C1-C3 alkyl groups. Other appropriate spacer monomers include vinyl ester, vinyl alcohol, maleic anhydride, propylene glycol and ethylene glycol.

As for cationic amines, there exist primary amines, secondary amines and tertiary amines depending on a specific type and pH of the composition. In general, secondary and tertiary amines, particularly tertiary amines are preferred.

Amine-substituted vinyl monomer and amines can be polymerized in the form of amine, and converted to ammonium through quaternization reaction.

Examples of appropriate cationic amino and quaternary ammonium monomer include vinyl compound substituted by dialkylaminoalkyl acrylate, dialkylaminoalkyl methacrylate, monoalkylaminoalkyl acrylate or monoalkylaminoalkyl methacrylate; trialkylmethacryloxyalkyl ammonium salt; trialkylacryloxyalkyl ammonium salt; diallyl quaternary ammonium salt; and a vinyl quaternary ammonium monomer having a cyclic cationic nitrogen-containing ring such as pyridinium, imidazolium and quaternary pyrrolidine. For example, there may be used alkyl vinyl imidazolinium and quaternized pyrrolidine, such as alkyl vinyl imidazolium, alkyl vinyl pyridinium and alkyl vinyl pyrrolidine salt. It is preferred that the alkyl parts of these monomers be lower alkyls such as C1-C3 alkyl, more preferably C1-C2 alkyl.

Examples of appropriate amine-substituted vinyl monomer used here include dialkylaminoalkyl acrylate, dialkylaminoalkyl methacrylate, dialkylaminoalkyl acrylamide and dialkylaminoalkyl methacrylamide. And, it is preferred that the alkyl group be C1-C7 hydrocarbon, more preferably C1-C3 alkyl.

The cationic polymer used here may include a mixture of monomer units derived from an amine- and/or quaternary ammonium-substituted monomer; and/or from a compatible spacer monomer.

Examples of an appropriate cationic polymer are as follows.

Copolymer of 1-vinyl-2-pyrrolidine and 1-vinyl-3-methyl imidazolium salt (e.g. chloride salt) (referred to as Polyquaternium-16 by Cosmetic, Toiletry and Fragrance Association, "CTFA"). This is, for example, commercially available under the product name of LUVIQUAT (e.g. LUVIQUAT FC 370) by BASF Wyandotte Corp. (Parsippany, N.J., USA).

Copolymer of 1-vinyl-2-pyrrolidine and dimethylaminoethyl methacrylate (referred to as Polyquaternium-11 by CTFA). This is, for example commercially available under the product name of GAFQUAT (e.g. GAFQUAT 755N) by ISP Corporation (Wayne, N.J. USA).

Cationic diallyl quaternary ammonium-containing polymer. This may include dimethyl diallyl ammonium chloride homo polymer; and copolymer of acryl amide and dimethyl diallyl ammonium chloride, which are respectively referred to as Polyquaternium 6 and Polyquaternium 7 by CTFA.

A mineral acid salt of aminoalkyl ester of homo and copolymer of unsaturated carboxylic acid having 3 to 5 carbon atoms, as disclosed in U.S. Pat. No. 4,009,256.

Other cationic polymers that can be used include a polysaccharide polymer such as a cationic cellulose derivative and a cationic starch derivate. Examples of the cationic polysaccharide polymer substance suitable for use in this case, include those expressed by the following formula:

[Chemical formula 1]

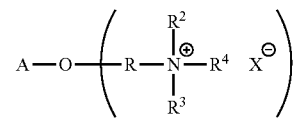

(In the formula, A represents an unhydroglucose residue such as an unhydroglucose residue of starch or cellulose; R represents an alkyleneoxyalkylene group, a polyoxyalkylene group or a hydroxyalkylene group or a combination thereof; $R^2$, $R^3$ and $R^4$ independently represent an alkyl group, an aryl group, an alkylaryl group, an arylalkyl group, an alkoxyalkyl group or an alkoxyaryl group, each group having at most 18 carbon atoms and the total number of the carbon atoms in each cationic part (i.e. the total number of the carbon atoms of $R^2$, $R^3$ and $R^4$) being preferably not more than 20; $X^-$ represents an anionic counter ion of, for example, halide such as $Cl^-$ and $Br^-$, acetate, phosphate, nitrate and alkyl sulfate.)

Cationic cellulose is available from Amerchol Corp. (Edison, N.J., USA) under the series of Polymer JR™ and LR™, as a salt of hydroxyethyl cellulose obtained through the reaction with trimethyl ammonium-substituted epoxide, which is referred to as Polyquaternium 10 by CTFA. Other types of cationic cellulose include a polymerizable quaternary ammonium salt of hydroxyethyl cellulose obtained through the reaction with lauryldimethyl ammonium-substituted epoxide, which is referred to as Polyquaternium 24 by CTFA. These substances are available from Amerchol Corp. (Edison, N.J., USA) under the product name of Polymer LM-200.

Other cationic polymers that can be used here include a cationic guar gum derivative such as guar hydroxypropyltrimmonium chloride (commercially available from Celanese Corp. as TM Jaguar series). Other substances include quaternary nitrogen-containing cellulose ether (e.g. as that disclosed in U.S. Pat. No. 3,962,418 quoted and incorporated as a part of this specification) and a copolymer of etherified cellulose and starch (as that disclosed in U.S. Pat. No. 3,958,581 quoted and incorporated as a part of this specification).

Although a cationic polymer is water soluble, it does not need to be soluble in a shampoo composition. However, it is preferred that such cationic polymer be either soluble in a shampoo composition; or soluble in a complex coacervate phase in a shampoo composition formed of a cationic polymer and an anionic substance. The complex coacervate phase of a cationic polymer is formed by an anion surfactant that can be optionally added to the composition or by an anionic polymer (e.g. sodium polystyrene sulfonate).

The formation of coacervate is dependent on various conditions such as molecular weight, concentration, interactive ionic substances, ion strength (including e.g. change in ion strength due to addition of salt), charge densities of cationic and anionic species, pH and temperature. The impact of such parameters on a coacervate system is discussed in "Anionic and Cationic Compounds in Mixed System" by J. Caelles et al, Cosmetic & Toiletries, Vol. 106, April 1991, pages 49 to 54; "Coacervation, Complex Coacervation and Flocculation" by C. J. Van Oss, J. Dispersion Science and Technology, Vol 9 (5,6), 1988-89, pages 561 to 573; and "Practical analysis of complex coacervate systems" by D. J. Burgess, J. Colloid and Interface Science, Vol, 140, No. 1, November 1990, pages 227 to 238.

It is particularly favorable when the cationic polymer exists in shampoo as a coacervate phase; or when a coacervate phase is formed on or from hair at the time of using shampoo or rinsing. A complex coacervate can adhere to hair more easily. Therefore, it is usually preferred that the cationic polymer exist in shampoo as a coacervate phase; or that such cationic polymer form a coacervate phase when diluted. When a coacervate is not already present in shampoo, it is preferred that the cationic polymer exist in the form of a complex coacervate in the shampoo when diluted by water preferably at a water:shampoo composition ratio of about 20:1, more preferably about 10:1, even more preferably about 8:1.

Techniques for analyzing the formation of complex coacervate are known in this industry. For example, at any selected dilution stage, microscopy analysis can be performed on a shampoo composition to identify whether a coacervate phase has been formed. Such coacervate phase may be identified as an additionally emulsified phase in the composition. The usage of a dye helps distinguish a coacervate phase from other insoluble phases dispersed in the composition.

It is preferred that the cationic polymer be selected from a group of hydroxyalkyl cellulose ether and a cationic guar gum derivative. Particularly preferable cationic polymers are Jaguar C13S, Jaguar C15, Jaguar C17, Jaguar C16 and Jaguar C162. Other preferable cellulose ethers are Polymer JR400, JR30M and JR125.

It is preferred that the cationic polymer be added to the cosmetic preparation of the present invention in an amount of 0.01 to 5% by mass, more preferably 0.05 to 1% by mass, even more preferably 0.08 to 0.5% by mass.

<Other Components>

Examples of other components used to prepare the cosmetic preparation of the present invention (cosmetic material preparation components) are as follows. That is, these components include, but are not limited to (1) hydrocarbons such as liquid paraffin, vaseline, solid paraffin, squalane and olefin oligomer; (2) esters such as isopropyl palmitate, stearyl stearate, octyl dodecyl myristate, octyl dodecyl oleate, acetylated lanolin and 2-ethylhexanoic acid triglyceride; (3) higher alcohols such as lauryl alcohol, cetyl alcohol, stearyl alcohol, lanolin alcohol and bees wax; (4) higher fatty acids such as palmitic acid and stearic acid, and amines such as diethanolamine for neutralizing said higher fatty acids; (5) moisturizers such as ethylene glycol, propylene glycol, 1,3-butylene glycol, glycerin and sorbitol; (6) inorganic powders such as titanium oxide, carbon black, iron oxide, sericite, talc, kaolin and mica; (7) organic polymer powders such as nylon, polyethylene and poly (metha) acrylic acid ester; (8) solvents such as water and ethanol; (9) the non-ionic surfactant, anion surfactant, cationic surfactant and amphoteric surfactant listed as the examples of (b) surfactant; (10) preservative agents, antifungal agents and pH adjusters; (11) coloring agents; (12) fragrances; (13) water-soluble polymers such as pectin guar gum, guar gum, xanthan gum, tamarind gum, carrageenan, carboxymethyl cellulose, starch, soluble starch, dextrin, α starch, sodium alginate, gum arabic, gelatin, tragacanth gum, locust bean gum, casein, lignosulfonate, carboxymethyl cellulose sodium salt, methyl cellulose, hydroxyethyl cellulose, carboxymethylated starch sodium salt, hydroxyethylated starch, starch phosphate ester sodium salt, polyvinyl alcohol, polyvinyl methyl ether, polyacrylamide, polyacrylate sodium salt, a copolymer of partially saponified vinyl acetate and vinyl ether, acrylic acid, methacrylic acid, a polymer or copolymer of maleic acid and an ester or salt thereof, hydroxypropyl cellulose (HPC), hydroxypropyl methyl cellulose, polyvinyl pyrrolidone and a vinyl pyrrolidone-vinyl acetate copolymer; and (14) ultraviolet absorbing agents.

<Intended Use>

Examples of the cosmetic preparation include hair cosmetic preparations such as hair oils, hair dyeing materials, combing oils, set lotions, stick pomades, Japanese traditional hair oils, hair creams, hair tonics, hair liquids, hair spray, pomades, shampoos, hair rinses, hair conditioners, hair lotions and split hair preventing agent; and skin cosmetic preparations such as hand creams, hand lotions, skin creams, foundations, eye shadows, eye liners, mascaras, face wash materials and antiperspirants.

WORKING EXAMPLE

Measurement and evaluation methods are as follows.

Average Particle Diameter of Emulsion:

Measured were values of median diameters on volume bases, using a laser diffraction scattering type particle size measuring device LA-920 (HORIBA, Ltd.).

Viscosity of organopolysiloxane as raw material having silanol group on molecular chain terminal:

The viscosities were measured using an Ostwald viscometer at 25° C., i.e. the viscosities measured were kinetic viscosities at 25° C.

Viscosity of Organopolysiloxane (Extraction Viscosity):

Isopropyl alcohol of 300 g was added to the prepared emulsion composition of 300 g while performing stirring, followed by sorting out only the dimethylsiloxane precipitated and then drying the same at 105° C. for 3 hours. Here, the viscosities were measured using a rotatory viscometer at 25° C., i.e. the viscosities measured were absolute viscosities at 25° C.

Amount of Octamethylcyclotetrasiloxane Contained in Emulsion:

The prepared emulsion composition of 0.1 g was subjected to extraction (three-hour shaking) using 10 ml of acetone containing tetradecane in an amount of 20 ppm by mass as an internal reference, followed by leaving the same overnight, and then collecting the acetone layer to perform gas chromatography analysis thereon, thus allowing the quantity of each Dn (low molecular cyclosiloxane) to be determined.

Stability:

The sample prepared was placed into a glass bottle of a volume of 100 ml, and was then left at 50° C. for a month before externally observing the same. Symbols of "○" represent examples where the stability was so favorable that the emulsion had exhibited no separation, i.e. a uniform and single phase. Symbols of "Δ" represent examples where the emulsion had slightly exhibited oil floating. Symbols of "x" represent examples where the stability was so unfavorable that the emulsion had exhibited a separation into two phases.

Feeling of Use:

The feeling of use was point-rated by 20 panelists and was evaluated based on an average score.

5: Very Good 4: Good 3: Normal 2: Bad 1: Very Bad

Base Emulsion

<Emulsion A>

With respect to 100 parts by mass of an organopolysiloxane (containing octamethylcyclotetrasiloxane in an amount of not more than 50 parts by mass) having a viscosity of 5,000 mm$^2$/s and a silanol group(s) on its molecular chain terminals, a homodisper was used to emulsify 0.75 parts by mass of polyoxyethylene (4 mol) lauryl ether, 2.25 parts by mass of polyoxyethylene (23 mol) lauryl ether, 4.0 parts by mass of dodecylbenzene sodium sulfonate and 4.2 parts by mass of water. Water was then added to the first emulsion thus obtained in an amount of 81.2 parts by mass, followed by using a homomixer to dilute and disperse the same. The emulsion obtained was then turned to 0° C., followed by adding a concentrated hydrochloric acid thereto in an amount of 1.2 parts by mass to perform emulsion polymerization. Later, a sodium carbonate solution of 10% by mass was added to the emulsion obtained in an amount of 6.4 parts by mass to neutralize the same, thus obtaining the target emulsion composition. The properties of such emulsion were such that the extraction viscosity was 2,000,000 mPa·s; the amount of D4 contained in the emulsion was 500 ppm by mass; and the average particle diameter was 170 nm.

<Emulsion B>

Cyclic siloxane of 50 parts by mass, dodecylbenzene sulfonic acid of 2.84 parts by mass and water of 45.66 parts by mass were mixed together to prepare an o/w emulsion, followed by treating the same with a high-pressure homogenizer. Later, emulsion polymerization was performed, and a sodium carbonate solution of 10% by mass was then used in an amount of 5.21 parts by mass to perform neutralization, thus obtaining the target emulsion composition. The properties of this emulsion were such that the extraction viscosity was 2,000,000 mPa·s; the amount of D4 contained in the emulsion was 35,000 ppm by mass; and the average particle diameter was 200 nm.

<Emulsion C>

D6 was added and mixed into the emulsion A in an amount of 150 ppm by mass to prepare an emulsion C.

<Emulsion D>

D5 was added and mixed into the emulsion A in an amount of 200 ppm by mass to prepare an emulsion D.

<Emulsion E>

D5 and D6 Were added and mixed into the emulsion A respectively in an amount of 300 ppm by mass and an amount of 150 ppm by mass to prepare an emulsion E.

All of the abovementioned emulsions are described in the following Table 1.

Cosmetic Preparation

Shampoo

A shampoo was prepared by mixing together the base emulsion of 3 parts by mass; polyoxyethylene (2 mol) lauryl ether sodium sulfate of 16 parts by mass; cocoamidopropyl betaine of 2.1 parts by mass; a cationic guar gum derivative (Jaguar C13S) of 0.1 parts by mass; Carbopol® 980 of 0.4 parts by mass; and an ion-exchanged water of 78.4 parts by mass.

Hand Lotion

A hand lotion was prepared by mixing together the base emulsion of 11.0 parts by mass; cetyl alcohol of 2.0 parts by mass; sorbitan monomyristate of 1.2 parts by mass; polyoxyethylene (25 mol) monostearate of 1.3 parts by mass; acetylated lanolin of 2.0 parts by mass; magnesium aluminum silicate of 1.5 parts by mass; a fragrance of 0.5 parts by mass; and an ion-exchanged water of 80.5 parts by mass.

Rinse

A rinse was prepared by mixing together the base emulsion of 10 parts by mass; distearate ethylene glycol of 3 parts by mass; cetanol of 2 parts by mass; monostearate propylene glycol of 3 parts by mass; monostearate glycerin of 3.8 parts by mass; polyoxyethylene (3) stearate of 3.8 parts by mass; acetyl chloride trimethylammonium of 5 parts by mass; polyoxyethylene (20) cetyl ether of 2 parts by mass; 1,3-butanediol of 5 parts by mass; methylparaben of 0.2 parts by mass; and an ion-exchanged water of 62.2 parts by mass.

Hair Set Lotion

A hair set lotion was prepared by mixing together the base emulsion of 5 parts by mass; hydroxyethyl cellulose of 0.2 parts by mass; ethanol of 10 parts by mass; a fragrance of 0.2 parts by mass; and an ion-exchanged water of 84.6 parts by mass.

Working Example 1a

The emulsion A was used to prepare the shampoo having the aforementioned composition. The shampoo thus obtained exhibited a favorable preservation stability and a favorable feeling of use.

Working Example 1b

The emulsion C was used to prepare the shampoo having the aforementioned composition. The shampoo thus obtained exhibited a favorable preservation stability and a favorable feeling of use. However, its feeling of use was slightly inferior to that of the working example 1a.

Working Example 1c

The emulsion D was used to prepare the shampoo having the aforementioned composition. The shampoo thus obtained exhibited a favorable preservation stability and a favorable feeling of use. However, its feeling of use was slightly inferior to that of the working example 1b.

Working Example 1 d

The emulsion E was used to prepare the shampoo having the aforementioned composition. The shampoo thus obtained exhibited a favorable preservation stability and a favorable feeling of use. However, its feeling of use was slightly inferior to that of the working example 1a.

Comparative Example 1

The emulsion B was used to prepare the shampoo having the aforementioned composition. Both the preservation stability and feeling of use of the shampoo thus obtained were inferior to those of the working examples 1a, 1b, 1c and 1d.

Working Example 2

The emulsion A was used to prepare the hand lotion having the aforementioned composition. The hand lotion thus obtained exhibited a favorable preservation stability and a favorable feeling of use.

Comparative Example 2

The emulsion B was used to prepare the hand lotion having the aforementioned composition. Both the preservation stability and feeling of use of the hand lotion thus obtained were inferior to those of the working example 2.

Working Example 3

The emulsion A was used to prepare the rinse having the aforementioned composition. The rinse thus obtained exhibited a favorable preservation stability and a favorable feeling of use.

Comparative Example 3

The emulsion B was used to prepare the rinse having the aforementioned composition. Both the preservation stability and feeling of use of the rinse thus obtained were inferior to those of the working example 3.

Working Example 4

The emulsion A was used to prepare the hair set lotion having the aforementioned composition. The hair set lotion thus obtained exhibited a favorable preservation stability and a favorable feeling of use.

Comparative Example 4

The emulsion B was used to prepare the hair set lotion. Both the preservation stability and feeling of use of the hair set lotion thus obtained were inferior to those of the working example 3.

The evaluation results of the abovementioned working examples and comparative examples are shown in Table 2.

TABLE 1

|  | Emulsion A | Emulsion B | Emulsion C |
| --- | --- | --- | --- |
| Siloxane viscosity(mPa · s) | 2,000,000 | 2,000,000 | 2,000,000 |
| D3(ppm by mass) | 20(3%) | <10 | 20(2.4%) |
| D4(ppm by mass) | 500(74.6%) | 20900(49%) | 500(61%) |
| D5(ppm by mass) | 100(14.9%) | 14410(33.8%) | 100(12.2%) |
| D6(ppm by mass) | 50(7.5%) | 4780(11.2%) | 200(24.4%) |
| D7(ppm by mass) | <10 | 1430(3.4%) | <10 |
| D8(ppm by mass) | <10 | 510(1.2%) | <10 |
| D9(ppm by mass) | <10 | 380(0.9%) | <10 |
| D10(ppm by mass) | <10 | 250(0.6%) | <10 |
| Σ D3~D10(ppm by mass) | 670 | 42660 | 820 |
| Particle diameter(nm) | 170 | 200 | 170 |

|  | Emulsion D | Emulsion E |
| --- | --- | --- |
| Siloxane viscosity(mPa · s) | 2,000,000 | 2,000,000 |
| D3(ppm by mass) | 20(2.3%) | 20(1.8%) |
| D4(ppm by mass) | 500(57.5%) | 800(71.4%) |
| D5(ppm by mass) | 300(34.5%) | 250(22.3%) |
| D6(ppm by mass) | 50(5.7%) | 50(4.5%) |
| D7(ppm by mass) | <10 | <10 |
| D8(ppm by mass) | <10 | <10 |
| D9(ppm by mass) | <10 | <10 |
| D10(ppm by mass) | <10 | <10 |
| Σ D3~D10(ppm by mass) | 870 | 1120 |
| Particle diameter(nm) | 170 | 170 |

% inside the brackets represent % by mass of each Dn contained in the total amount of D3 to D10
<10 are not included in the calculation of Σ D3~D10

TABLE 2

|  | Preservation stability | Feeling of use |
| --- | --- | --- |
| Working example 1a | ○ | 4.5 |
| Working example 1b | ○ | 4.1 |
| Working example 1c | ○ | 3.9 |
| Working example 1d | ○ | 4.2 |
| Comparative example 1 | Δ | 3.1 |
| Working example 2 | ○ | 4.5 |
| Comparative example 2 | Δ | 3.2 |
| Working example 3 | ○ | 4.0 |
| Comparative example 3 | Δ | 3.1 |
| Working example 4 | ○ | 4.4 |
| Comparative example 4 | Δ | 3.3 |

It is understood from the above tables that the cosmetic preparation of the present invention exhibits a superior preservation stability and feeling of use when it contains an emulsion having D4 in an amount of not larger than 1,000 ppm by mass.

The invention claimed is:

1. A cosmetic preparation comprising an (a) organopolysiloxane emulsion in an amount of not smaller than 0.1% by mass, wherein the (a) organopolysiloxane emulsion is prepared by:
   (I) obtaining a first emulsion composition by emulsifying a mixture comprising
   (A) 100 parts by mass of an organopolysiloxane expressed by a formula (1) and comprising 1,000 ppm by mass or less of octamethylcyclotetrasiloxane $$HO(R^1_2SiO)_nH \qquad (1)$$

wherein each $R^1$ independently represents a hydrogen atom or a substituted or unsubstituted hydrocarbon group having 1 to 20 carbon atoms; and n represents a number that yields a kinetic viscosity of the organopolysiloxane of 3,000 to 100,000 mm$^2$/s at 25° C.
   (B) 1 to 100 parts by mass of a non-ionic surfactant
   (C) 1 to 100 parts by mass of an anion surfactant
   provided that a range of mass ratio of component (B): component (C) is 25:75 to 50:50 and
   (D-1) 1 to 10 parts by mass of water; and then
   (II) adding no water or adding
   (D-2) not larger than 100,000 parts by mass of water;
   to the first emulsion composition, followed by performing emulsion polymerization in the presence of at least one catalyst selected from the group consisting of (i) a catalyst comprising the anion surfactant (C), and (ii) an (E) acid catalyst, at a temperature of −15 to 5° C.

2. The cosmetic preparation according to claim 1, wherein octamethylcyclotetrasiloxane as D4 occupies not smaller than 60% by mass of a total amount of hexamethylcyclotrisiloxane as D3 to eicosamethylcyclodecasiloxane as D10 in the (a) organopolysiloxane emulsion obtained through emulsion polymerization.

3. The cosmetic preparation according to claim 1, wherein a total amount of hexamethylcyclotrisiloxane as D3 to eicosamethylcyclodecasiloxane as D10 in the (a) organopolysiloxane emulsion obtained through emulsion polymerization is not larger than 1,000 ppm by mass.

4. The cosmetic preparation according to claim 1, wherein an average particle diameter of the (a) organopolysiloxane emulsion is not larger than 300 nm.

5. The cosmetic preparation according to claim 1, further comprising
   (b) a surfactant; and
   (c) a cationic polymer, in addition to (a).

6. A hair cosmetic preparation comprising the cosmetic preparation according to claim 1.

* * * * *